(12) United States Patent
Jaroszeski et al.

(10) Patent No.: US 6,355,485 B1
(45) Date of Patent: Mar. 12, 2002

(54) ELECTROFUSION CHAMBER

(75) Inventors: Mark J. Jaroszeski; Richard A. Gilbert; Richard Heller, all of Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/616,084

(22) Filed: Jul. 14, 2000

Related U.S. Application Data

(63) Continuation-in-part of application No. 09/328,833, filed on Jun. 8, 1999.
(60) Provisional application No. 60/088,758, filed on Jun. 10, 1998.

(51) Int. Cl.$^7$ .......................... C12N 13/00; C12N 15/02
(52) U.S. Cl. .................. 435/449; 435/450; 435/451; 435/452; 435/453; 435/454; 435/173.1; 435/173.4; 435/173.5; 435/173.6; 435/173.7; 435/455; 435/461; 435/468; 435/471; 435/285.2

(58) Field of Search ................... 435/449, 450, 435/451, 452, 453, 454, 173.1, 173.4, 173.5, 173.6, 173.7, 455, 461, 468, 471, 285.2

(56) References Cited

PUBLICATIONS

Jaroszeski et al (Biophysical Journal, vol. 67, Oct. 1994, 1574–1581).
Jaroszeski, M.J., Gilbert, R.A., and Heller, R. (1994). *Analytical Biochemistry* 216:271–275.

*Primary Examiner*—James Ketter
(74) *Attorney, Agent, or Firm*—Kohn & Associates

(57) ABSTRACT

A new and useful apparatus for producing cell electrofusion is provided. The apparatus comprises:
  a. a chamber with a substrate disposed therein,
  b. means for directing the cells to be fused toward one side of the substrate; and
  c. a device for inducing fusion of the portion of the cells.

43 Claims, 4 Drawing Sheets

ELECTROFUSION CHAMBER

CROSSREFERENCE TO RELATED APPLICATIONS

This is a Continuation-In-Part of U.S. Ser. No.: 09/328,833, filed Jun. 8, 1999, which is a conversion of U.S. Provisional Application No.: 60/088,758 filed Jun. 10, 1998, both of which are incorporated herein by reference.

TECHNICAL FIELD

The present invention relates to an electrofusion chamber, and particularly to a disposable electrofusion chamber which is used to provide a simple, inexpensive and efficient way of performing electrofusion.

BACKGROUND

Electrofusion is the common name for procedures that induce fusion of living cells using electricity. Cell-cell electrofusion (CCE) is the generic term used to describe electrofusion of living cells. CCE can refer to fusion of one cell type to a different cell type, or it can refer to fusing cells of the same type. In this application, reference to fusion of cells is intended to encompass both fusion of different cell types and also fusion of the same cell types. Moreover, it is intended to encompass the fusion of two or more cells to each other.

CCE processes generally involve three principal steps. First, fusion partners (i.e., two or more cells to be fused to each other) must be forced into contact with each other between two electrodes or some other means of inducing electrofusion. The cells must be in an electrically conductive medium. Second, one or more electrical pulses are applied to the cells that are in contact between the electrodes. Electrical pulses induce fusion and are administered by creating and maintaining a potential (voltage) difference across the electrodes. CCE is usually achieved using direct current (DC) pulses. The third and final CCE step occurs naturally; fused cells anneal into one cell due to their normal fluidity. CCE processes do not normally yield 100% fusion. Typically, a fraction of the contacted cells are induced to fuse while the remaining fraction does not fuse. Also, many of the extensively used methods involve steps which have a high rate of cell killing.

Most existing commercial CCE devices and applications known to the applicants use a process called dielectrophoresis to cause cell—cell contact. Dielectrophoresis is the application of alternating current (AC) to cause fusion partners to line up in chains between the electrodes. Thus, cell—cell contact is achieved at the points where adjacent cells in a chain are touching. Dielectrophoresis is incorporated into the first step of the three-step fusion process described above. After chains have formed, one or more DC pulses are delivered to induce fusion and the cells are allowed to anneal.

Jaroszeski et al., (Biophysical Journal, Vol. 67, Oct. 1994, 1574–1581) discloses apparatus and methods developed to enable mechanically facilitated cell—cell electrofusion to be performed. The apparatus and methods mechanically place cells in contact before fusion. A novel fusion chamber is disclosed composed of two functionally identical electrodes that are housed in a multi-layer structure. The layers function as a support for the electrodes. They also allow adjustment of the distance between opposing electrode faces. The electrodes were constructed to allow cells to be deposited, by vacuum, onto each face. The electrode faces were positioned at a predetermined distance from each other to mechanically force cell—cell contact between the deposited cells. Fusion was induced by delivering direct current pulses to the juxtaposed cells.

Jaroszeski et al. (Analytical Biochemistry, 216, 271–275 (1994)) discloses a cytometric method for detecting and quantitating hybrid cells that resulted from cell—cell electrofusion. Cells from two different lines and two vital fluorescent dyes were used in conjunction with a flow cytometer to demonstrate the method.

The German Patent Publication DE 3505147 A1 to Strellrecht et al. discloses an electrofusion process wherein cells are fixed on a first and second carrier. The two carriers are arranged so that the cells that are fixed to the respective carriers are opposite relative to each other. The cells are moved toward each other forming pairs of cells, one from each carrier. The pairs are each fused.

It would be advantageous to provide more efficient and effective means for inducing cell-to-cell contact and fusion than that described above. The present invention provides improved means for inducing such cell—cell contact and uses electric pulses applied from a different direction relative to deposited cells than prior art.

SUMMARY OF THE PRESENT INVENTION

The present invention provides a new and useful electrofusion device which is designed to be a convenient, inexpensive, and easy-to-use device that can be used to force cell—cell contact and to induce fusion of at least a portion of the cells in cell-to-cell contact. This device can be produced as a single and/or multiple use device, it is easily sterilized, it can be made as a disposable device, and does not require the use of AC.

Fusion without AC has significant benefits. For example, an electrofusion device that requires only a DC generator represents a lower initial equipment investment than is generally required for dielectrophoresis equipment. Moreover, the high cost of generators that produce AC and DC may discourage some researchers from using electrofusion. The present invention solves that problem by requiring only DC voltage, thereby enabling performance of electrofusion without the AC generator costs associated with conventional dielectrophoresis devices.

Additionally, the device of the present invention is flexible, in the sense that it can be operated from the DC power supply of various electric cell manipulator devices. For example, many laboratories use a physical phenomenon that is related to fusion in order to manipulate cells. This phenomenon is called electroporation. Specifically, it is common for researchers to perform both electrofusion and electroporation. However, electric pulse generators for electroporation produce DC pulses only. Thus, an inexpensive electrofusion chamber that does not require AC makes electrofusion possible for facilities that already have DC pulse generators.

The fact that in both of the foregoing examples the need for AC is eliminated also has biological relevance. Specifically, other devices known to applicants utilize a phenomenon called dielectrophoresis induced by AC of relatively long duration (e.g. seconds and/or minutes) to achieve cell—cell contact. Elimination of long duration AC is biologically advantageous because it can directly cause cellular damage. Also, heat generated during dielectrophoresis can be damaging to the cells.

According to the present invention, an apparatus for producing electrofusion of two types of cells comprises:

a. chamber with a substrate that is used as a surface for achieving cell—cell contact, b. a mechanism for directing cells to be fused contained in a fluid medium toward one side of the substrate in such a manner that a substantial amount of cells are drawn to and retained against the one side of the substrate with a portion of the cells in cell-to-cell contact with each other along the one side of the substrate, and c. a device having chemical or chemical/energy means for inducing fusion of a portion of the cells in cell-to-cell contact with each other over the predetermined portion of the one side of the substrate.

The device for inducing fusion can be an energy source such as an electric field applied to the substrate or another energy source such as, but not limited to, sound/pressure waves, light microwaves, electromagnetic energy or any combination of these energy sources. It is also within the scope of the invention to include chemical fusing agents, either alone or in combination with an energy source, to effect the fusion process.

The means for drawing the cells toward one side of the substrate can be achieved in two preferable ways that both achieve the same result. The first employs a porous substrate and a vacuum source. The vacuum source is configured to apply a level of vacuum to the fluid medium that is sufficient to draw a significant portion of the fluid medium through the substrate while retaining the cells on one side of the substrate in cell-to-cell contact. The vacuum source is configured to induce this migration of the cells and also to retain enough medium mixed with the cells to preserve the viability of the cells to be fused. The second configuration employs a charged substrate with a selected polarity that will attract cells of opposite polarity to one side of the substrate.

The chamber is preferably designed so that it can be operated from the DC power source of a conventional dielectrophoresis device having both an AC current source and a DC voltage source. The device can also be operated from a DC power source of the type typically associated with an electroporation device, or from various other types of DC power sources found in other facilities.

These and other features of the present invention will become further apparent from the following detailed description and the accompanying drawings.

DETAILED DESCRIPTION

As described above, electrofusion is the common name for procedures that induce fusion of living cells using electricity. Cell—cell electrofusion (CCE) is the generic term used to describe electrofusion of living cells. CCE can refer to fusion of one cell type to a different cell type, or it can refer to fusing cells of the same type. In this application, reference to fusion of two types of cells is intended to encompass both fusion of different cell types and also fusion of the same cell types. Moreover, while the description below relates to fusion of two cells, it is contemplated that the principles of this invention can be used to fuse two or more cells.

Generally, electrofusion is performed by applying one or more direct current pulses to closely juxtaposed cells. Unipolar and bipolar pulses have been used. Pulses may be administered as a train of identical or different pulses. The currently accepted scientific explanation of CCE is based on the principle of dielectric breakdown. When a biological cell is subjected to electric fields, a transmembrane potential is induced. This induced potential is superposed on the naturally occurring transmembrane potential maintained by the cell. The natural potential is commonly called the resting potential. In physical terms, these potentials are ions that accumulate on either side of the membrane. Ions of one polarity are on one side, and ions of the opposite polarity are on the other side. If the potential across the membrane is high enough then the membrane will dielectrically break down as a result of the force of attraction between the separated ions of opposite polarity. This type of breakdown results in temporary structural defects in the lipid bilayer structure and depolarization of the membrane. The defects have been described as pores and pore-like structures because it has been observed that molecules that do not normally enter to cytosolic compartment can gain access to the cell interior after cells have been electrically treated. The structural defects are temporary as normal membrane fluidity enables cells to reseal membrane defects to regain an intact membrane. The fusion of two or more cells is facilitated by maintaining close cell-to-cell contact when cells are electrically treated so that membrane defects that occur in both cells in the area of contact will enable both cell membranes to reseal as one.

Figure 1A:
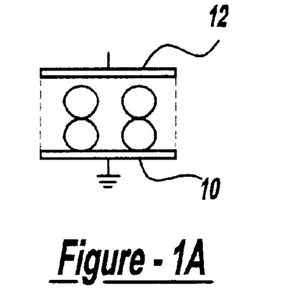
FIGS. 1a–1c schematically elaborate certain underlying principles of electrofusion.
Figure 1B:
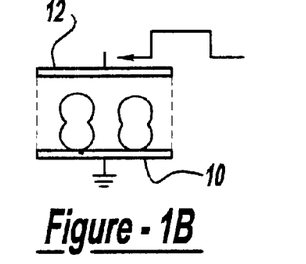
Figure 1C:
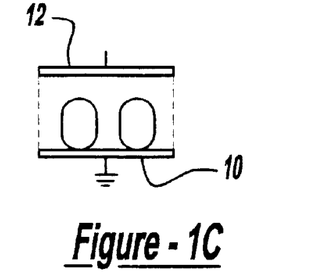

CCE processes generally involve three principal steps. Referring to FIG. 1a, fusion partners (i.e., two types of cells to be fused to each other) must be forced into contact with each other between two electrodes 10, 12. The cells must be in an electrically conductive medium. Second, one or more electrical pulses are applied to the cells that are in contact between the electrodes (see FIG. 1b). Electrical pulses induce fusion and are administered by creating and maintaining a potential (voltage) difference across the electrodes. CCE is usually achieved using direct current (DC) pulses. The third and final CCE step occurs naturally; fused cells anneal into one cell due to their normal fluidity (see FIG. 1c). CCE processes do not normally yield 100% fusion. Typically, a fraction of the contacted cells are induced to fuse while the remaining fraction does not fuse.

Figure 2:
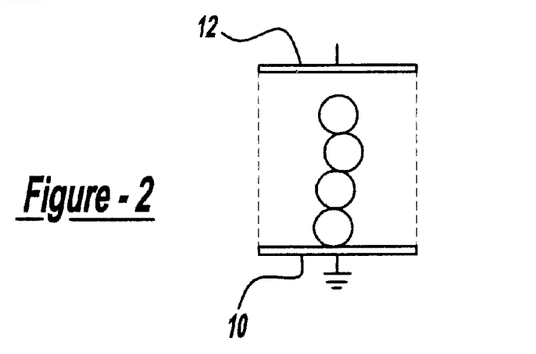
FIG. 2 schematically illustrates principles of a machine for performing dielectrophoresis.
Figure 3A:
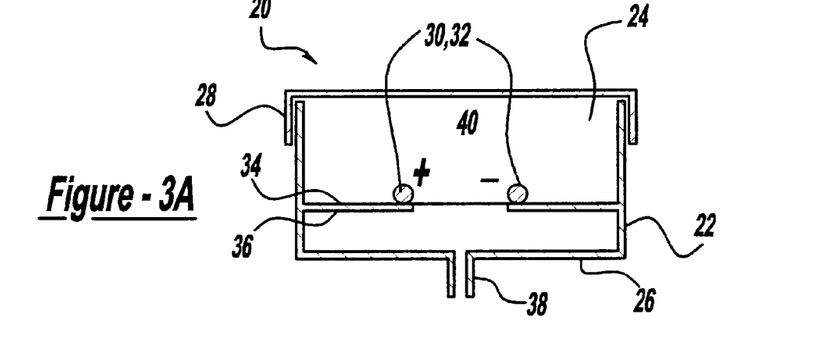
FIGS. 3A and 3B are schematic cross-sectional views of a device for performing electrofusion according to the principles of the present invention at 90 degrees to each other.
Figure 3B:
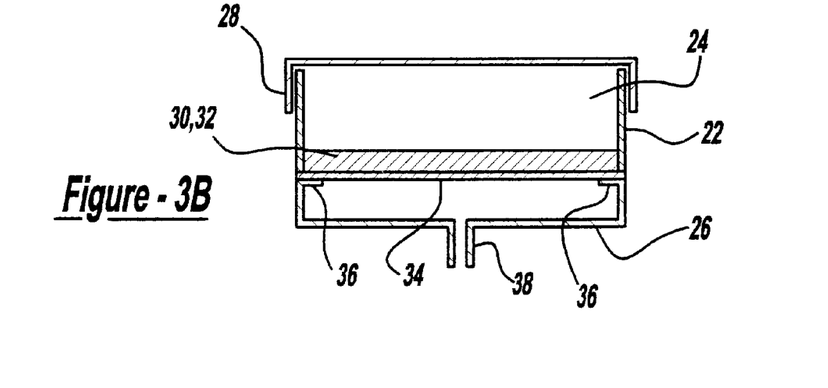

As illustrated in FIG. 2, with a typical dielectrophoresis machine, application of alternating current (AC) is used to cause fusion partners to line up in chains between the electrodes 10, 12. Thus, cell—cell contact is achieved at the points where adjacent cells in a chain are touching. After chains have formed, one or more DC pulses are delivered to induce fusion and the cells are allowed to anneal.

FIGS. 3A, 3B, 4, 5 and 7–9 show different views of a chamber 20 for performing electrofusion according to the principles of the present invention. The chamber 20 includes a molded chamber body 22 and a cap 28. The container 22 is cylindrical with an open top 24 and a bottom 26 and serves as a housing for the internal components. The cap 28 covers the top of the body 22 to complete the chamber 20. The internal components of the chamber 20 include two electrodes 30, 32, a porous substrate 34, a substrate support 36, and a port 38 for connection to a vacuum source. The chamber 20 can also include an O-ring 58 for perfecting a seal within the chamber 20.

Cell—cell electrofusion is conducted in the chamber 20 by first placing a suspension of cells between the two electrodes 30, 32. Then, vacuum is applied. The vacuum is sufficient to draw liquid from the suspension toward one side 40 of the substrate 34 and through the pores of the substrate, but not so complete as to evacuate all of the liquid medium, so that the cells in the suspension remain substantially viable. This draws deposits and maintains layers of cells on the one side 40 of the substrate. This will result in cells in contact with each other in the space between the two electrodes 30, 32. After deposition, one or more DC pulses are administered to the electrodes 30, 32 to induce fusion of cells that are in cell-to-cell contact between the electrodes. The electric field produced by the DC pulses will be substantially parallel to the substrate 34.

Figure 5:
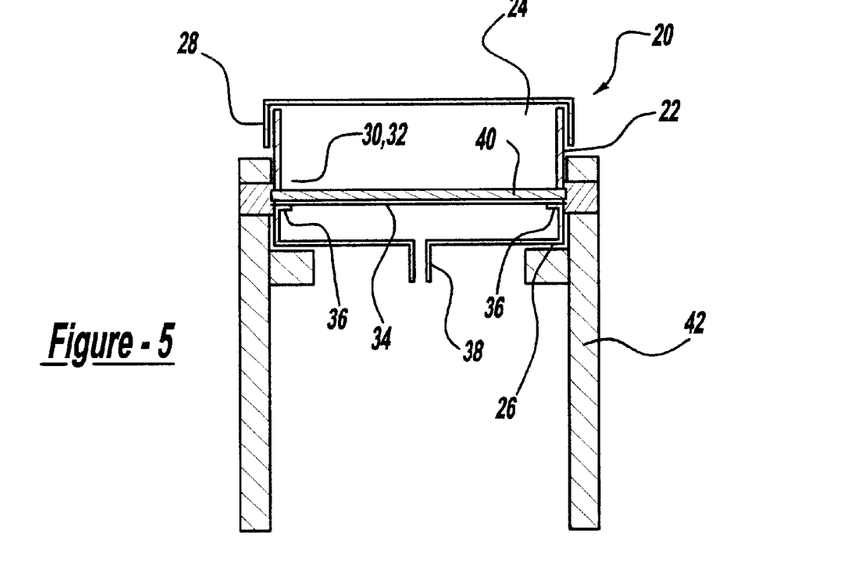
FIG. 5 is a schematic cross-sectional view of a chamber according to the present invention supported on a reusable stand, and further illustrates how electrical connections are made.

An additional feature of the invention is a reusable stand 42 that is designed to hold the chamber during use. The stand is depicted in FIG. 5. The stand is a means of holding the small chambers in a manner that allows easy access to the vacuum port and also a simple means of connecting an electrical generator to the chamber. A stand that fulfills these criteria also reduces the complexity and cost of the disposable chambers. This is because pulse generator connections and a means of holding the small chamber need not be built into the disposable chamber.

Figure 4:
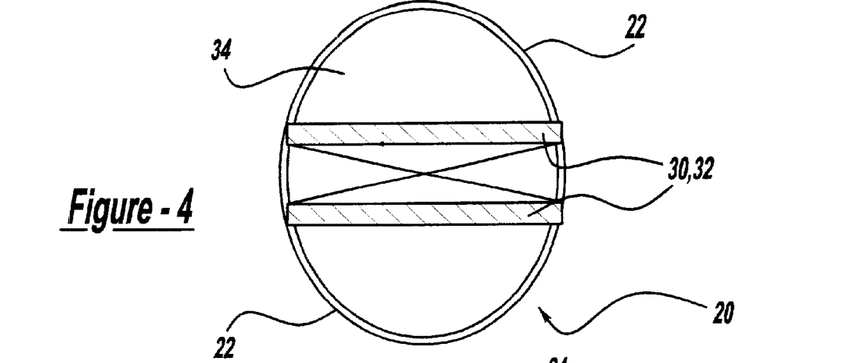
FIG. 4 is a schematic top view of the device of FIG. 3, taken from the direction 4—4.

The chamber described above is a very flexible and functional design that can be applied to many different situations. For example, as illustrated in FIGS. 3, 4 and 5, the container 22 is cylindrical, the porous substrate 34 is circular, and the electrodes 30, 32 extend across a portion of the container. However, it is contemplated that the container could have other geometric forms (e.g. it could be rectangular in cross section) and the substrate could have a configuration to match the configuration of the container. Moreover:

1. the physical size of the chamber can be adjusted to accommodate fusion of small numbers of cells or large number of cells;
2. the pore size and number of pores per unit area in the substrate can be adjusted, depending on the cell type under investigation;
3. electrode size and spacing can be adjusted to accommodate various electrofusion parameters. For example, a chamber can be designed with an electrode gap that is wide enough for only two mammalian cells to fit between them (approximately 20 micrometers). Performing fusion in this manner would greatly increase the yield of fusion products that consist of two cells.

An example of the way an electrofusion chamber can be built and operated to perform electrofusion is described below:

1. Mold, extrude, or machine the body of the chamber out of a nonelectrically conductive material such as plastic and which, when required, can be sterilized utilizing methods known in the art.
2. Provide a porous surface for deposition of cells. A mesh, porous membrane, or other porous material can be utilized. The applicants have utilized polycarbonate track etch membranes (Poretics Inc.).
3. Provide two or more electrodes for delivering electric pulses to the cells that are deposited on the porous surface. These can be of any shape or size. The inventors suggest parallel stainless steel electrodes that can be of circular or rectangular cross-sectional areas. These electrodes should be placed on the porous surface prior to cell deposition, placed immediately adjacent to the cells after deposition, embedded in the porous surface, and/or embedded in the substrate support.
4. Provide a vacuum source generated from a standard vacuum pump, suction bulb, or syringe. A means for attaching the vacuum source to the port for vacuum connection should also be provided. (No special characteristics of the vacuum pump.) Alternatively, pressure can be applied to the side of the chamber that contains the cells in order to cause or force migration of the cells toward one side of the membranes.
5. Provide a means for connecting a DC pulse generator to the electrodes.
6. Provide a DC generator that is capable of delivering current to the electrodes. Commercially available electroporation and electrofusion generators that deliver DC pulses can be used; however, use is not limited to these generators.

One way of operating the device is as follows:

1. Prepare a suspension of living biological cells containing one or more different types of cells that the user desires to fuse.
2. Remove cap from device and transfer a desired quantity of cells into the fusion chamber.
3. Apply vacuum to draw the cells into contact with each other on the porous membrane. The inventors have found that vacuums in the range of 25 to 150 mmHg are useful; however, other degrees of vacuum can be used.
4. Apply DC electricity to induce fusion between the juxtaposed cells. The exact electrical parameters for inducing fusion are dependent on the type(s) of cells that the user wishes to fuse. Some parameters that have been shown to work are: 1–10 rectangular pulses with pulse durations ranging from microseconds to milliseconds. The magnitude of the field generated in these cases ranges from hundreds of volts per centimeter to thousands of volts per centimeter.
5. After pulse delivery, fused cells are washed out of the chamber using a carrier solution such as, but not limited to, physiologic saline.

The prototype constructed and used as described above was used to fuse rat N1-S1 hepatocellular carcinoma cells (American Type Culture Collection, CRL-1604). Prior to introducing the cells into the chamber, one-half of the cells were stained with 5-chloromethylfluorescein (CMFDA, Molecular Probes, Eugene, Oreg.) which is a green fluorescing compound. The remaining half of the cells were stained with 5-(and 6)-(((4-chloromethyl)benzoyl)amino) tetramthylrhodamine (CMTMR, Molecular Probes) which is a red fluorescing compound. Equal parts of the green and red fluorescing cells were mixed together and then introduced into the fusion chamber. Fusion products were identified using flow cytometry as those hybrids that exhibited both red and green fluorescence (Jaroszeski, M. J., Gilbert, R. A., and Heller, R. (1994) Detection and quantitation of cell—cell electrofusion products by flow cytometry *Analytical Biochemistry* 216: 271–275). A table of resulting data is given below.

| Electrical Treatment | Mean Percent Dual Fluorescing Hybrids | Standard Deviation |
|---|---|---|
| No Pulses | 2.08 | 0.314 |
| 8 DC Pulses, 100 $\mu$s each, 1500 V/cm field strength | 5.62 | 3.44 |
| 8 DC Pulses, 100 $\mu$s each, 2000 V/cm field strength | 7.85 | 2.82 |
| 8 DC Pulses, 100 $\mu$s each, 3000 V/cm field strength | 9.08 | 6.64 |
| 4 DC Pulses, 100 $\mu$s each, 2000 V/cm field strength | 8.6 | 0.82 |
| 4 DC Pulses, 100 $\mu$s each, 3000 V/cm field strength | 5.52 | 3.21 |

Figure 6:
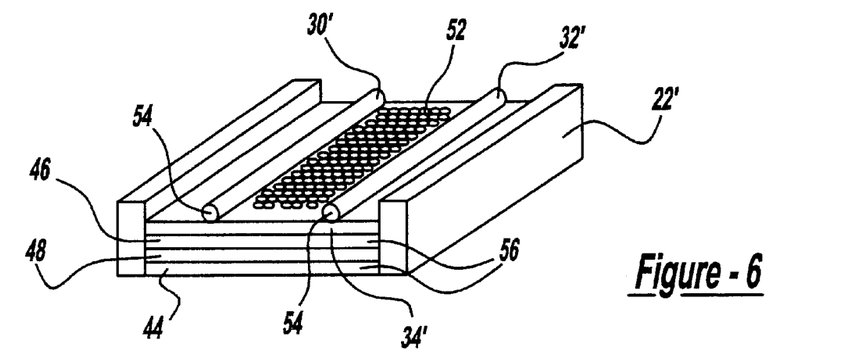
FIG. 6 is a schematic perspective view of a further embodiment of a chamber made in accordance with the present invention.

The above description applies to using an electrofusion chamber that employs a porous substrate and a vacuum source to cause cells to migrate to one side of a substrate to achieve cell-to-cell contact. As previously mentioned, a charged substrate 34' can be used to achieve migration and subsequent cell-to-cell contact, as shown in FIG. 6 (like primed numbers are used to show like members between the different embodiments shown). Most biological cells have a surface charge (negative). Providing a substrate 26' with a surface charge of opposite polarity (positive) causes migration from a fluid medium to the surface of the substrate 36'. A surface charge can be imparted on a substrate by means of an electrical and/or mechanical circuit. Surface charges are also a natural occurrence or imparted as part of a manufacturing process. The use and function of a fusion chamber that employs a charged substrate is similar to the description above except that no vacuum is applied.

Referring specifically to FIG. 6, the substrate 34' is comprised of conductive plates 44, 46 separated by a dielectric 48. Above the uppermost conductive plate 46 is a plate of non-conductive material 34' that serves as the substrate. The cells 52 are deposited in contact with each other between the two electrodes 30', 32', the electrodes delivering fusogenic pulses. A DC pulse generator 54 is operatively connected to the electrodes 30', 32' while means for providing a voltage 56 is operatively connected to the conductive plates 44, 46. Thusly, this embodiment of the invention provides a charged substrate as a surface for achieving cell-to-cell contact.

Figure 7:
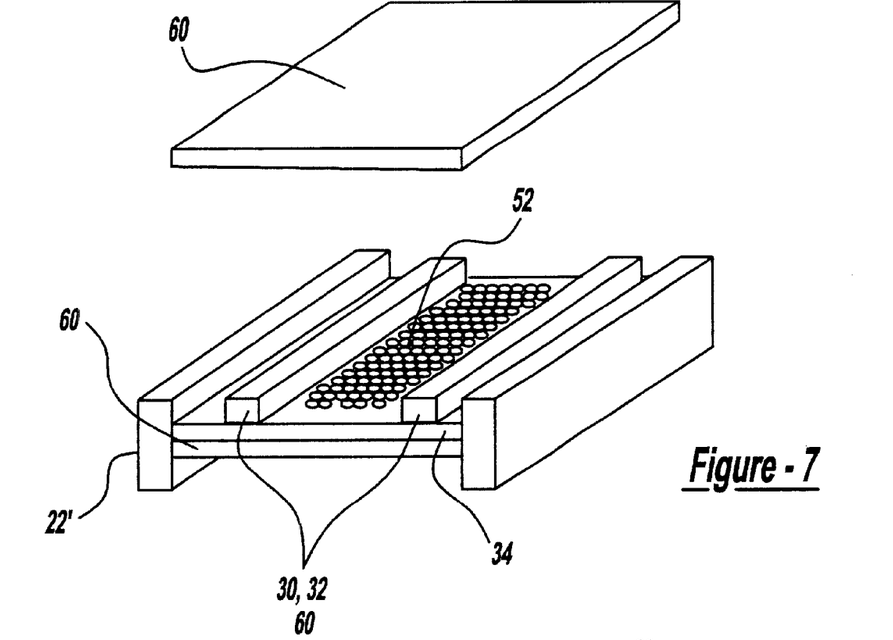
FIG. 7 is an expanded three dimensional depiction of the chamber of the instant invention, further showing the alternate embodiments of the invention.
Figure 8:
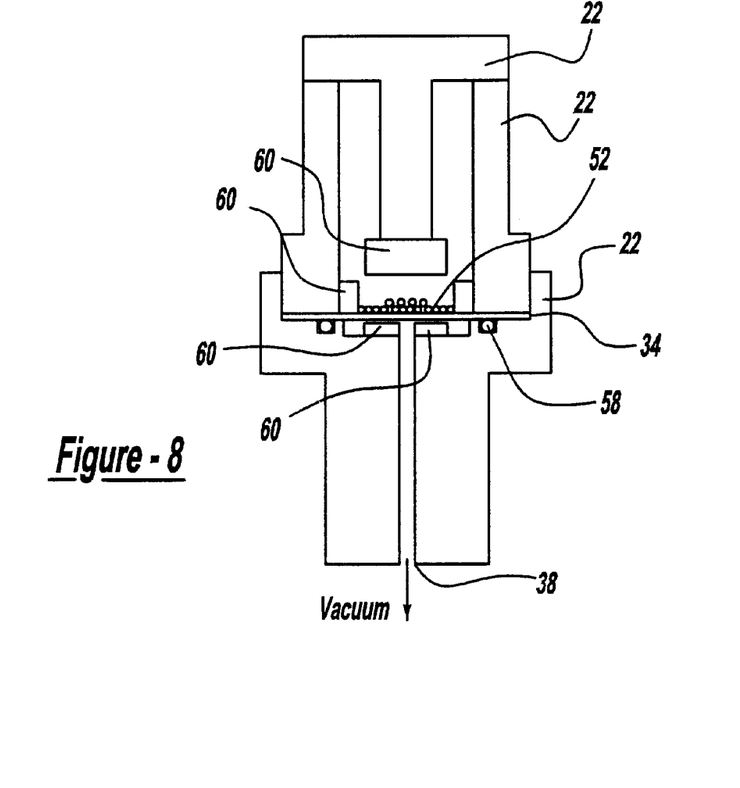
FIG. 8 is another schematic perspective view showing the further embodiments of the invention.
Figure 9:
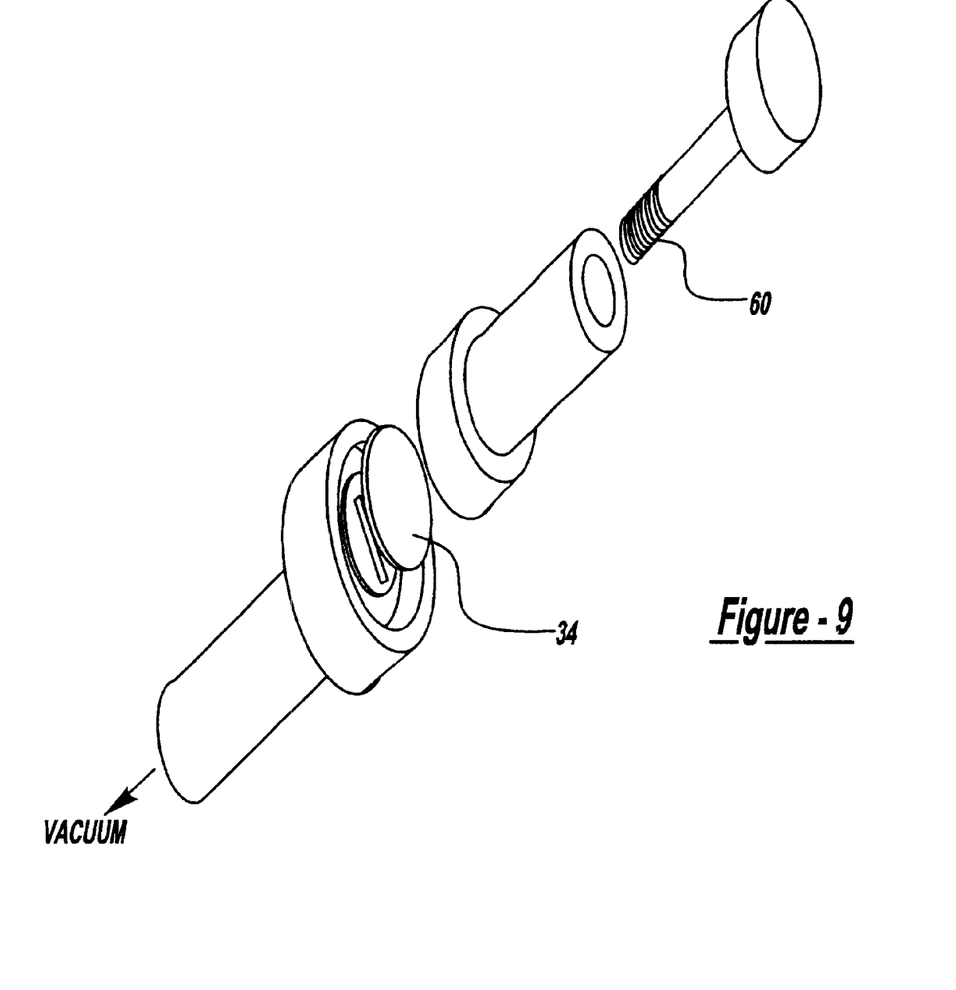
FIG. 9 is a composite view of the invention showing the further embodiments of the chamber made in accordance with the present invention.

Moreover, modifications to the electrofusion chamber described above can be made without departing from the concept of the present invention. For example, while vacuum and charged substrates are described for drawing cells to the one side of the substrate, it is contemplated that other devices (e.g. devices using magnetic bead separation principles) could be used to draw the medium containing the cells toward the one side of the substrate and hold the cells in cell-to-cell contact against the one side of the substrate while a fusogenic DC potential is applied to those cells. In addition, rather than drawing the cell containing medium to the substrate, all containing medium can be pressurized to force it against the substrate. Although the invention has been described in terms of electric fields to effect the fusion process, it is also within the scope of the invention to use other forms of fusion techniques 60 that are commonly known to those of ordinary skill in the art. Referring to FIGS. 7–9, these techniques 60 can include, but are not limited to, sound/pressure waves, light, microwaves, electromagnetic energy, magnetically induced electric fields or any combination of these sources. Also contemplated within the scope of the invention is the use of chemical agents, such as, but again not limited to, polyethylene glycol, biological glues and various surface active agents. In addition, any combination of both chemical and energy-based techniques 60 is within the scope of the invention.

For example, the sound/pressure waves can be applied using commercially available sound transducers 60 (FIGS. 7–9) or other types of sound emitting devices known in the art. These devices 60 are typically driven by an electrical signal generator such as a sinusoidal voltage signal. These generators emit sound that is within a frequency range of 1 Hertz to 10 Gigahertz. The sound energy can be by one or more emitters located within the device and/or in proximity to the device. Sound energy can be within the range of $1 \times 10^{-5}$ Watts per meter squared (W/m2) and 50 Watts per meter squared (W/m2) which is typically quantitated at the output of a sound emitting device. This type of energy can be delivered continuously or in a pulsatile manner. By pulsatile is meant that energy is applied for a period of time and then discontinued, this is followed by subsequent time periods of energy application and time periods when no energy is applied. The total time that energy is applied in a continuous manner can range from microseconds to minutes. The time that sound energy is applied in a pulsatile manner can range from microseconds to tens of minutes.

In another example, light energy can be applied using one or more commercially available light emitters located within or in proximity to the fusion chamber. An example of a suitable light emitting device but is not limited to, a laser emitting source. When used in combination with a chemical agent, other suitable light sources such as UV sources can be used to effect bonding of UV-sensitive chemicals. Light sources are commercially available and can emit in any spectral region desired including, but not limited to the infrared, ultraviolet, and visible spectrum. Pulsed laser energy or continuous laser energy can be applied for a period of time in the range of microseconds to minutes.

In a further embodiment, microwave radiation can be applied using commercially available technology such as, but not limited to, waveguides. One of these devices can be located within and/or in proximity to the fusion chamber in order to transmit the energy to the cells in the chamber. Microwave energy can be applied in a continuous manner or in a pulsed manner for a time period ranging from microseconds to minutes. The frequency range of the microwave energy can be within the range of 100 megahertz to 100 gigahert, with the energy applied to the cells being in the range of 1×10–12 watts per meter squared. This energy can also be applied in a pulsatile or continuous manner for times that are on the order of microseconds to minutes.

It is also further provided by the present invention that a chemical source can also be used to effect the fusion process. These are also chosen from the commonly known chemical fusion agents known to those of skill in the art and include, but are not limited to, polyethylene glycol, chemical glues, surface active agents and other self-curing or curable agents commonly known in the art that bond cells or analogous materials together. This chemical fusion can also be combined with any of the above energy source either singularly or in any suitable combination.

Additionally, the cells can be exposed to the energy source or chemical source prior to being introduced into the chamber. Fusion takes place after migration, but is still being promoted by the disruption of the cell membrane prior to insertion into the chamber itself.

The energy and/or chemical fusion source can be applied or added sequentially or simultaneously and in any combination. Thus, for example, one energy source can be used to disrupt the cell membranes and a second can be used to complete the fusion process. Alternatively, a chemical source can also be used with other chemical sources or in combination with energy sources and introduced at the same time, or before, or after use of the energy sources. Therefore, any combination of fusion sources, and any manner of timing for application of the source is considered within the scope of the invention.

Based on the above, the present invention is distinguishable from the prior art. Based on the prior art, cells are deposited on two porous surfaces (as set forth in the patents cited in the background art section above), the surfaces are moved together, and an electric field (DC pulses) is applied in the direction that is perpendicular to the plane of the substrates used for deposition. According to the present invention, cells are deposited onto one substrate surface and pulses are applied in a direction that is parallel to the surface of the substrate. This provides a simpler design to practice the process in that it is easier to use the present invention. It is also much simpler to make, as the prior art requires a very precise movement mechanism and measurement of gap between two surfaces with cells on them. The present invention includes no moving parts and no dimensions that are critical down to the micron level as required by the prior art.

Further, points of fusion in the present invention take advantage of the areas of cell-to-cell contact of adjacent cells in the same plane as the substrate. The prior art requires multiple layers of cells sandwiched between two substrates. Finally, the present invention can be made with much less cost due to lack of moving parts and critical dimensions compared to the prior art assemblies. The present invention can be made disposable whereas the prior art would be far too costly to be disposable. This is critical in practicing the invention in an environment that requires sterility which is best facilitated by a single use disposable device.

Accordingly, there has been described above an electrofusion chamber which is believed to be simple and efficient, and which, according to the preferred embodiment, does not require an AC generator. However, it is believed possible to utilize an AC generator to achieve cell-to-cell fusion, using the chamber and other principles of the present invention, if the AC generator is utilized for very short time periods (e.g. less than seconds), so as not to cause the biological problems described above. With the foregoing disclosure in mind, it is believed other forms of electrofusion chambers embodying the principles of the present invention will become apparent to those in the art.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A method of effecting cell—cell fusion comprising the steps of (a) providing a chamber with a substrate and a fluid medium containing cells, (b) migrating at least some of the cells toward one side of the substrate, and (c) fusing a portion of the migrated cells in cell-to-cell contact in proximity to the one side of the substrate, wherein said fusing occurs energetically, chemically and by combinations thereof.

2. The method of claim 1, wherein said fusing step is further defined as effectuating fusion by energy means.

3. The method of claim 2, wherein the energy means is selected from the group consisting of sound/pressure waves, light, microwaves or electromagnetic energy and magnetically induced electric fields.

4. The method of claim 1, wherein the fusing step is further defined as effectuating fusion by chemical means, wherein the chemical means is selected from the group consisting of polyethylene glycol, chemical glues, surface active agents, self-curing agents and curable agents.

5. The method of claim 1, wherein said fusion step is further defined preliminarily fusing a portion of the migrated cells prior to the cells being introduced into the chamber.

6. The method of claim 1, wherein said fusing step is further defined as simultaneously applying a plurality of fusing steps.

7. The method of claim 1, wherein said fusing step is further defined as being a plurality of fusing steps applied sequentially.

8. An apparatus for producing cell fusion, comprising:
   (a) a chamber having a substrate,
   (b) a fluid medium for containing cells to be fused in said chamber,
   (c) means for inducing migration of cells in said chamber toward one side of said substrate, and
   (d) means for inducing fusion of at least a portion of the cells.

9. The apparatus of claim 8, wherein said fusion means is selected from the group consisting essentially of an energy means, a chemical means and a combination of chemical and energy means.

10. The apparatus of claims 8 or 9, wherein said energy means is selected from the group consisting of sound/pressure waves, light, microwaves or electromagnetic energy and magnetically induced electric fields.

11. The apparatus of claim 9, wherein said chemical means is selected from the group consisting of polyethylene glycol, chemical glues, surface active agents, self-curing and curable agents.

12. The apparatus of claims 8 or 9, further including fusion means housed outside said chamber such that fusion takes place prior to the cells being introduced into said chamber.

13. The apparatus of claims 8 or 9, wherein said fusion means includes a plurality of fusion means applied simultaneously.

14. The apparatus of claims 8 or 9, wherein said fusion means includes a plurality of said fusion means applied sequentially.

15. A method of modifying cell membranes comprising the steps of:
   (a) providing a chamber with a substrate and a fluid medium containing cells;
   (b) migrating at least a portion of the cell toward one side of the substrate, and
   (c) applying a cell membrane modifying technique to the cell's membrane in proximity to the one side of the substrate.

16. The method of claim 15 wherein said applying step includes applying a modifying technique selected from the group consisting of application of energy, a chemical and combinations thereof.

17. The method of claim 16, wherein said applying step includes applying energy in a form selected from the group consisting essentially of sound/pressure waves, light, microwaves or electromagnetic energy and magnetically induced electric fields.

18. The method of claim 16, wherein said applying step includes applying a chemical in a form selected from the group consisting of polyethylene glycol, chemical glues, surface active agents, self-curing and curable agents.

19. The method of claim 15, wherein said applying step includes applying a technique which allows the fluid medium to enter the cells.

20. The method of claim 15, wherein said applying step includes applying a cell modifying technique which causes at least a part of the fluid medium to attach to the membranes.

21. The method of claim 15, wherein said applying step includes applying a cell modifying technique which causes at least a part of the fluid medium to be inserted into the membranes.

22. The method of claim 15, wherein said applying step includes applying a modifying technique which causes molecules present in the cell to exit the cell.

23. The method of claim 15, wherein said applying step includes applying a modifying technique which causes molecules present in the cells to exit the cell and allowing the fluid material to enter the cell, thereby effecting a material exchange.

24. The method of claim 23, wherein said effecting step includes sequentially effecting a material exchange.

25. The method of claim 23, wherein said effecting step includes simultaneously effecting a material exchange.

26. The method of claim 15, wherein said applying step includes sequentially applying a cell modifying technique which applies a plurality of fusion devices.

27. The method of claim 15, wherein said applying step includes simultaneously applying a cell modifying technique which applies a plurality of fusion devices.

28. The method of claim 15, wherein said applying step includes preliminarily applying a cell modifying technique prior to the cells being introduced into the chamber.

29. The method of claim 15, wherein said applying step includes applying a cell modifying technique in the chamber prior to at least a portion of the cells being migrated toward one side of the substrate.

30. An apparatus for producing cell membrane modifications, comprising:

(a) a chamber having a substrate,
(b) a fluid medium for containing, effecting changes to cells or combinations thereof,
(c) means for inducing migration of at least a portion of cells toward on the side of the substrate, and
(d) means for applying a cell modification technique to cells in proximity to one side of the substrate.

31. The apparatus of claim 30, wherein the modification technique means is selected from the group consisting of an energy means, chemical means, and combinations thereof.

32. The apparatus of claim 31, wherein the energy means is selected from the group consisting essentially of sound/pressure waves, light, microwaves or electromagnetic energy and magnetically induced electric fields.

33. The apparatus of claim 31, wherein the chemical means is selected from the group consisting essentially of polyethylene glycol, chemical glues, surface active agents, self-curing and curable agents.

34. The apparatus of claim 30, wherein the cell modification means allows the fluid medium to enter the cells.

35. The apparatus of claim 30, wherein the cell modification means causes at least a part of the fluid medium to attach to the cell membranes.

36. The apparatus of claim 30, wherein the cell modification means causes at least a part of the fluid medium to be inserted into the cell membranes.

37. The apparatus of claim 30, wherein the cell modification means causes molecules present in the cell to exit the cell.

38. The apparatus of claim 30, wherein the cell modification means causes both molecules present in the cells to exit the cell as well as allowing the fluid material to enter the cell, thus effecting a material exchange.

39. The apparatus of claim 30, wherein the cell modification means effects a sequential material exchange.

40. The apparatus of clam 30, wherein the cell modification means effects a simultaneous material exchange.

41. The apparatus of claim 30, wherein the cell modification means consists of a plurality of fusion means applied sequentially.

42. The apparatus of claim 30, wherein the cell modification means consists of a plurality of fusion means applied simultaneously.

43. The apparatus of claim 30, further including the cell modification means housed outside the chamber such that the modification takes place prior to the cells being introduced into the chamber.

* * * * *